(12) United States Patent
Shah

(10) Patent No.: US 7,470,251 B2
(45) Date of Patent: *Dec. 30, 2008

(54) GASTRO-OCCLUSIVE DEVICE

(76) Inventor: Tilak M. Shah, 104 Lochberry La., Cary, NC (US) 27511

( * ) Notice: Subject to any disclaimer, the term of this patent is extended or adjusted under 35 U.S.C. 154(b) by 0 days.

This patent is subject to a terminal disclaimer.

(21) Appl. No.: 11/273,065

(22) Filed: Nov. 14, 2005

(65) Prior Publication Data
US 2006/0129094 A1 Jun. 15, 2006

Related U.S. Application Data

(63) Continuation of application No. 10/854,550, filed on May 26, 2004, now Pat. No. 7,112,186.

(51) Int. Cl.
*A61M 29/00* (2006.01)
(52) U.S. Cl. .............. 604/96.01; 604/104; 604/174; 604/509; 604/910
(58) Field of Classification Search .......... 604/96.01, 604/97.01, 97.02, 98.01, 98.02, 104, 264, 604/508, 509, 907, 910, 912, 915, 920, 174, 604/175
See application file for complete search history.

(56) References Cited

U.S. PATENT DOCUMENTS 4,311,146 A * 1/1982 Wonder .................. 605/195
4,464,175 A 8/1984 Altman et al.
5,234,454 A * 8/1993 Bangs .................... 606/191
5,527,280 A * 6/1996 Goelz .................... 604/99.02
5,807,333 A 9/1998 Osborne et al.
5,833,915 A 11/1998 Shah
6,270,477 B1 * 8/2001 Bagaoisan et al. ....... 604/96.01
6,460,541 B1 10/2002 Shah et al.
6,663,646 B1 12/2003 Shah
6,712,832 B2 3/2004 Shah
6,960,199 B2 * 11/2005 Burkett et al. .............. 604/514
7,112,186 B2 * 9/2006 Shah ....................... 604/96.01
7,172,613 B2 * 2/2007 Wazne .................... 606/192

* cited by examiner

*Primary Examiner*—Kevin C Sirmons
*Assistant Examiner*—Bhisma Mehta
(74) *Attorney, Agent, or Firm*—Vincent K. Gustafson; Intellectual Property/Technology Law

(57) ABSTRACT

A gastro-occlusive device, comprising a balloon disposable in a stomach cavity of a patient, and inflatable therein to occlude a portion of the volume of the stomach cavity, a gas flow tube coupled at a distal end thereof with the balloon and extending outwardly through a stomach wall for coupling with a gas source for selectively inflating the balloon, to occlude at least a portion of the volume of the stomach cavity. The gastro-occlusive device may be employed in combination with a feeding tube unit, a drain unit or other ancillary apparatus, and is useful for treatment of morbid obesity and various eating disorders.

20 Claims, 2 Drawing Sheets

GASTRO-OCCLUSIVE DEVICE

CROSS-REFERENCE TO RELATED APPLICATIONS

This is a continuation of U.S. patent application Ser. No. 10/854,550 for "Gastro-Occlusive Device" filed on May 26, 2004 in the name of Tilak M. Shah, issued Sep. 26, 2006 as U.S. Pat. No. 7,112,186.

BACKGROUND OF THE INVENTION

1. Field of the Invention

This invention relates to a gastro-occlusive device, such as is useful for the treatment of morbid obesity and a variety of eating disorders.

2. Description of the Related Art

World-wide public health surveys and nutritional studies reflect a currently high and growing incidence of obesity in many countries.

The reasons for such pervasiveness of overweight individuals are numerous and include progressively increasing levels of sedentary behavior, ubiquity of processed high-fat, high-carbohydrate foods, increased automation of formerly manual activities, and decreased attention to physical fitness and exercise.

Although substantial efforts have been undertaken individually, governmentally and societally to ameliorate and reverse this trend, involving novel diets, food supplements, exercise equipment, nutritional regulations, psychological and counseling-based approaches, engineered foods, and many other interventional actions, such efforts have failed to address this serious and growing problem.

This problem is particularly serious in the case of individuals who are severely overweight (e.g., who exceed weight averages of applicable height/weight norms by 50% or more). For this segment of the overweight population, surgical intervention has been an increasingly preferred mode of resolving issues of excessive body weight. So-called "stomach stapling," as a species of gastric reduction surgery, has become common as a mode of treatment of morbid obesity. This intervention involves closing off an upper portion of the stomach so that ingestion of small amounts of food produces satiety. In the surgical process termed vertical banded gastroplasty, the stomach is stapled vertically with rows of staples producing a reduced stomach volume typically constituting only a few tenths of a liter. A band then may be stapled to both walls of the stomach to prevent the stomach from stretching and to control the size of the stomach outlet. The stomach thereby is made smaller in volume, causing the patient to eat less while achieving a feeling of fullness, i.e., satiety.

Gastric reduction surgery has significant associated risks that impact its use and reliability. The stomach after the surgical procedure is still able to stretch, and staples can break and require additional emergency surgical intervention, since the detached staples may pose a life-threatening condition. Additionally, there are major side-effects to the surgery, including death, stroke, diarrhea, nausea, vomiting, chronic heartburn, and vitamin deficiencies. A significant portion of individuals who undergo gastric reduction surgery require a second operation to correct the side effects. There are other forms of gastric surgery, including laparoscopic adjustable gastric banding, which likewise has significant post-operative side effects.

Thus, although gastric reduction surgery is effective in many instances to provide a reduction in food intake and consequently of weight of the individual, it nonetheless carries significant health and safety risks that limit its use as a treatment option for morbid obesity.

It would therefore be a significant advance in the art to provide an alternative to gastric reduction surgery for the treatment of morbid obesity, which avoids the associated health and safety risks of conventional gastric reduction surgery.

SUMMARY OF THE INVENTION

The present invention relates to a gastro-occlusive device.

In one aspect, the present invention relates to a gastro-occlusive device, comprising a balloon disposable in a stomach cavity of a patient, and inflatable therein to occlude a portion of the volume of the stomach cavity, a gas flow tube coupled at a distal end thereof with the balloon and extending through a stomach wall to a proximal end that is at or in interior proximity to a surface of the patient's body or extends exteriorly out of the patient's body, and means for selectively inflating the balloon, coupled to the gas flow tube at the proximal end thereof and arranged to flow inflation gas to the balloon in the patient's stomach cavity, for said inflation therein to occlude at least a portion of the volume of the stomach cavity.

In another aspect, the invention relates to a method of treating a subject in need of treatment for an eating disorder or overweight condition, said method comprising disposing in the stomach of the subject a balloon that is inflatable to occlude at least a portion of interior volume of the stomach, wherein the balloon is coupled by a gas flow passage to an actuatable source of inflation gas, and actuating the source of inflation gas to flow gas into the balloon for inflation thereof to occlude at least a portion of the interior volume of the stomach, to an extent producing satiety with reduced intake of nutrition, relative to a corresponding subject lacking the inflated balloon in the subject's stomach.

Other aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1:
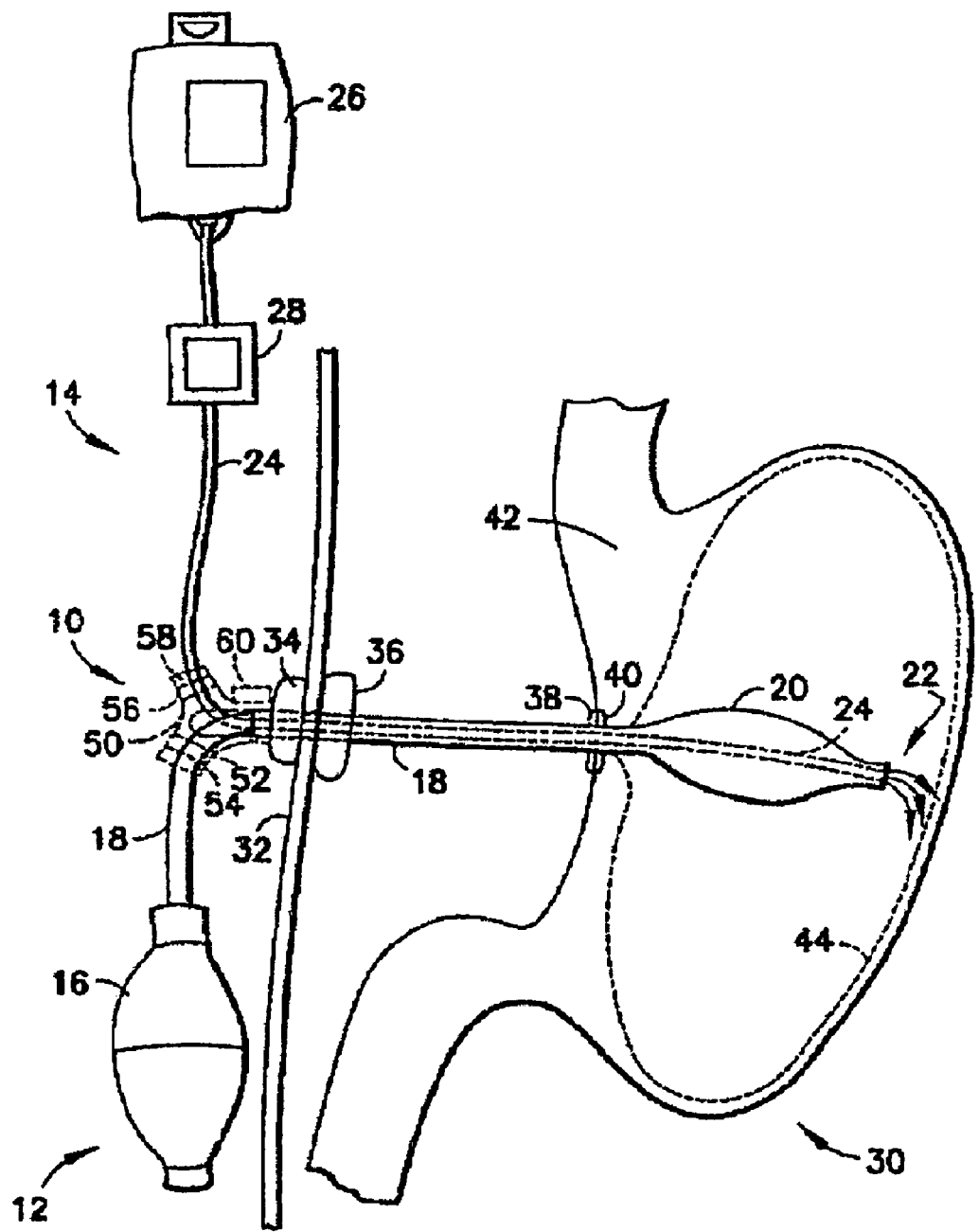
FIG. 1 is a schematic view of a gastro-occlusive device, with an optional feed tube assembly according to one embodiment of the invention.

The present invention is based on the discovery that a gastro-occlusive device can be formed as an inflatable balloon article for positioning in the stomach of a patient in need of gastric reduction for combating overeating, wherein the inflatable balloon article positioned in the stomach cavity and coupled with exteriorly disposed structure allowing selective inflation and deflation of the balloon article to adjust the working volume of the stomach.

By selective inflation, the user can cause the expanded volume of the balloon article to occupy a major portion of the stomach volume, whereby satiety is achieved in a manner analogous to gastric reduction surgery, but without the necessity of banding or stapling the stomach, with the attendant side effects and risks of such surgery.

The stomach may for example have a volume of 1.5 liters and a capacity of 3 liters when expanded. By disposing an inflatable balloon article in the stomach cavity that is selectively inflatable to occlude a major fraction of such stomach volume, e.g., at least 50%, at least 75%, at least 95%, or up to even 100% occlusion levels, the ingestion of food necessary to reach satiety is correspondingly reduced. If necessary for nutritional or medical reasons, the balloon can be selectively deflated, or alternatively maintained in an inflated state with periodic reinflation of the balloon as needed to maintain the expanded volume for occlusion of the stomach volume.

The invention in another embodiment utilizes the inflatable balloon occlusive device in combination with a feeding tube, drainage tube or other additional device, in an assembly providing for selective variation of the operative stomach volume and ingress/egress of material as needed.

In one specific embodiment, the feeding tube can be refunctionally deployed as a withdrawal tube to withdraw material from the stomach, subsequent to feeding, to assist the limitation of nutritional material to the patient.

The disclosures of U.S. Patent Application Publication No. 2005/0015047A1 published Jan. 20, 2005 in the name of Tilak M. Shah for "INFLATABLE DUAL BALLOON CATHETER," U.S. Patent Application Publication No. 2005/0222329A1 published Oct. 6, 2005 in the name of Tilak M. Shah for "EXTRUSION LAMINATE POLYMERIC FThM ARTICLE AND GASTRIC OCCLUSIVE DEVICE COMPRISING SAME," U.S. Pat. No. 6,712,832 issued Mar. 30, 2004 in the name of Tilak M. Shah for "LOW-PRESSURE MEDICAL BALLOONS AND METHOD OF MAKING SAME," U.S. Pat. No. 6,663,646 issued Dec. 16, 2003 in the name of Tilak M. Shah for "ISOTROPICALLY EXPANSIBLE BALLOON ARTICLES USEFUL IN IN VIVO LUMENAL PROCEDURES AND METHOD OF MAKING SUCH BALLOON ARTICLES," U.S. Pa. No. 6,460,541 issued Oct. 8, 2002 in the names of Tilak M. Shah and Deszo K. Levius for "HEAT-SEALED INFLATABLE ARTICLE AND METHOD OF MAKING SAME," and U.S. Pat. No. 5,833,915 issued Nov. 10, 1998 in the name of Tilak M. Shah for "METHOD OF WELDING POLYURETHANE THIN FILM," hereby are incorporated herein in their respective entireties, for all purposes, and are jointly referred to hereinafter as the "Shah, et al. Patent Disclosures."

The balloon article can advantageously be formed as a gas barrier film structure constituting a laminate including a layer of sealing film, having main top and bottom surfaces; and a layer of thermoplastic polymer film, laminated (e.g., extrusion laminated) to the layer of sealing film, on at least one of the main top and bottom surfaces, in which the sealing film has a composition and thickness imparting gas barrier character to the multilayer film and wherein the layer(s) of thermoplastic polymeric material alone lacks such gas barrier character, as more fully described in the aforementioned U.S. patent application Ser. No. 10/815,282 filed Apr. 1, 2004 in the name of Tilak M. Shah for "EXTRUSION LAMINATE POLYMERIC FILM ARTICLE AND GASTRIC OCCLUSIVE DEVICE COMPRISING SAME."

The balloon may be fabricated as more fully described in the aforementioned U.S. Pat. No. 6,712,832 issued Mar. 30, 2004 in the name of Tilak M. Shah for "LOW-PRESSURE MEDICAL BALLOONS AND METHOD OF MAKING SAME," in which a low-pressure medical balloon is fabricated by providing a thin film of thermoplastic polymeric material that is heated to a sufficient temperature for vacuum forming thereof. A first half-section for the balloon is formed by subjecting the thermoplastic polymeric film to vacuum suction. A second half-section for the balloon then is formed by subjecting a same or different thermoplastic polymeric thin film to vacuum suction, following which the first half-section of the balloon is bonded to the second half-section along respective edges thereof to yield the balloon.

Additionally, or alternatively, the balloon article can be fabricated and can be constituted materials-wise, as more fully otherwise described in the Shah et al. Patent Disclosures.

Referring now to the single drawing, FIG. 1 is a schematic view of a gastro-occlusive device according to one embodiment of the invention.

The gastro-occlusive device and feed tube assembly 10 includes a gastro-occlusive device 12, and is optionally in combination with a feeding tube unit 14 (or other additional device such as a drain tube). The gastro-occlusive device 12 includes an inflatable balloon 20 at the distal end of gas tube 18, as illustrated. The balloon and the gas tube may be separately formed and subsequently coupled with one another, e.g., by RF welding, adhesive bonding, etc., or alternatively the balloon and the gas tube may be integrally formed as a single-piece item by extrusion, blow molding, dip molding, casting, etc.

The balloon 20 is formed of a film material, e.g., of polyurethane, silicone or other polymeric material, e.g., synthetic elastomer, and is fabricated in any suitable manner, as for example as variously described in the Shah et al. Patent Disclosures. The gas tube 18 may be formed of a same or different material. The balloon may be formed in any suitable manner, including, without limitation, film welding, dip molding, blow molding, LIM molding, rotomolding, or any other suitable technique appropriate to the material of construction.

The balloon 20 is shown disposed in a deflated state in the stomach cavity 42 of the stomach 30 of a patient, with the gas tube 18 coupled to the balloon, and extending through the wall of the stomach 30, being retained in position by exterior flange member 38 and interior flange member 40, which may be interlocking with one another, or otherwise secured in relation to the stomach wall as stomach wall positional anchoring members, insert adapted for placement along inner and outer surfaces, respectively, of the stomach wall, so as to keep the gas tube 18 sealed in passage through the stomach wall, and fixedly positioned (it being understood that normal movement of the stomach will occur, along with contraction and expansion of the stomach due to the peristaltic musculature thereof).

The gas tube 18 extends outwardly from the stomach and through the dermal wall 32 shown schematically in FIG. 1. The gas tube is positionally secured at the dermal wall 32 by exterior flange member 34 and interior flange member 36, which as in the case of flange members 38 and 40, may be interlocking with one another as dermal wall positioning anchoring members, adapted for placement along outer and inner surfaces, respectively, of the dermal wall, or otherwise secured in anchoring relation to the dermal wall, so as to keep the gas tube 18 sealed in passage through the dermal wall, and fixedly positioned (it being understood that normal movement of the dermal wall will likewise occur). As shown in FIG. 1, spacing is provided between the outer stomach wall positional anchoring member 38 and the inner dermal wall positional anchoring members 36, with a section of the gas tube 18 disposed therebetween.

Optionally, the gas tube 18 in a specific embodiment extends exteriorly of the patient's body as illustrated, and is connected to a squeeze bulb 16. The squeeze bulb 16 can be manually repetitively squeezed in a pumping fashion to flow air from the ambient environment of the patient into the gas tube 18 for flow therethrough into the balloon 20, for inflation of the balloon from the deflated state depicted in the drawing, to the inflated state shown by dashed line 44. In the inflated state, with the balloon expanded to the volume indicated by the dashed line 44, the balloon occludes most of the stomach cavity volume.

Alternatively to the use of a squeeze bulb as illustrated, the balloon occlusive device may feature the gas tube as having the associated structure shown in dashed line representation in FIG. 1, pursuant to which the gas tube terminates at a coupling member 52 in cap 50, to which a matably engageable coupling 54 having a tube segment and squeeze bulb associated therewith, can be attached. In this manner, the squeeze bulb can be selectively attached to and removed from the coupling member 52 of the cap 50. Alternatively, such coupling 52 may be constructed for engagement with a gas supply at a physician's office or in a care facility, so that the inflation and deflation of the balloon is controlled by a medical practitioner, to avoid any patient compliance issues. The elimination of an always-connected squeeze bulb also improves the ease of use and lifestyle of the patient.

With the balloon in the inflated state, the patient can ingest food in a normal manner, but due to the restricted volume of the stomach due to the occlusive character of the balloon, the patient will experience rapid onset of satiety, as the ingested food fills the limited stomach volume.

Subsequent to onset of satiety and loss of the hunger impulse by the patient, the balloon 20 can be deflated from its inflated state indicated by dashed line 44, to the deflated state indicated in solid line representation in the FIG. 1 drawing. For example, the squeeze bulb 16 may be constructed with a stop-cock or valve on its proximal end, which can be adjusted by the patient or a medical assistant to permit the squeeze bulb to be switched to an evacuation mode, for pump-down of the balloon in the patient's stomach.

Alternatively, as noted, the coupling 52 may be adapted for attachment to a dedicated air or other gas supply administered by a physician or other healthcare personnel, to avoid any issues of patient non-compliance.

Alternatively, the balloon may be retained in the inflated state for an extended period of time, to provide ongoing occlusive action by the balloon in the stomach of the patient, and restrict the intake of food by the patient for a sustained period of time.

The balloon article and associated inflation/deflation means and connecting tubing and positioning means, as above described, may be provided as a unitary device in one embodiment of the invention.

Optionally, as illustrated, an additional device, such as the illustrated feeding tube unit 14, or alternatively a drain tube or other structure or device, may additionally be provided.

It will therefore be appreciated that the drawing of the inventive system in FIG. 1 has been drawn to show both the balloon article and the feeding tube unit, for economy of illustration, as schematically depictive of both (1) the embodiment of the invention wherein the balloon article and associated infrastructure for inflation and deflation, without provision of the feeding tube unit, and (2) an optional embodiment of the invention wherein the balloon article and associated infrastructure for inflation and deflation are provided in combination with a feeding tube unit.

The feeding tube unit 14 as illustratively shown in FIG. 1 includes a tube 24 which in the specific depicted embodiment is joined in fluid supply relationship at its proximal end to the fluid supply bag 26. The tube 24 extends through a sidewall of the gas tube 18 as shown and distally thereof is interiorly disposed in and coaxial with the gas tube 18. Thus, the tube 24 extends through the lumen of gas tube 18 to the distal end 22 of the balloon 20, at which terminus the tube 24 has an open end, permitting the efflux from the tube 24 of fluid flowed through the tube 24 from the fluid supply bag, under the action of the pump 28, which may be of any suitable type, e.g., a peristaltic pump.

The feeding tube unit 14 therefore may be arranged to actuate the pump 28 and flow nutrient fluid from the bag 26 though tube 24 to the open distal end 22 of the balloon, when the balloon is in a deflated condition, and with subsequent inflation of the balloon serving to close such open distal end 22 by the pressure of the inflation air introduced into the balloon by the action of the squeeze bulb 16. For such purpose, the distal end 22 may be formed with a self-sealing valve, e.g., of the type described in U.S. Pat. No. 6,460,541 issued Oct. 8, 2002 in the names of Tilak M. Shah and Deszo K. Levius for "HEAT-SEALED INFLATABLE ARTICLE AND METHOD OF MAKING SAME." Alternatively, the feeding tube unit may be arranged to flow nutritive material to the stomach when the balloon is inflated, so that there is no "pinch-off" effect exerted on the tube at its open end by the inflated balloon.

The gastro-occlusive device and feed tube assembly 10 shown in FIG. 1 may also be constructed and arranged so that the pump 28 is reversible in character, and that when the balloon is deflated and the stomach cavity contains nutrient material, the stomach contents can be pumped out of the stomach cavity by exertion of suction at the open distal end 22 of the balloon 20. In such reverse mode of operation, in place of the fluid supply bag 26, a collection reservoir may be provided, for collection and final disposition of the evacuated contents of the stomach cavity.

Further, although the tube 24 is shown as being internally disposed in the gas tube 18, it will be appreciated that the tube 24 may be externally disposed on the surface of the gas tube, or otherwise part of a double lumen tube, having respective passages connecting with fluid supply and inflation gas supply means.

As a still further alternative, the gastro-occlusive device assembly may comprise a triple lumen or other multi-lumen tube, in which one lumen is connected to the fluid supply bag, or to a drain, another is connected or connectable to the squeeze bulb or other air supply means, and a third connects to a small ancillary balloon to anchor the gas tube (gas supply catheter) to the skin wall, and such third lumen for such purpose connects or is connectable to the air supply means.

As mentioned, the occlusive device in lieu of a squeeze bulb 16 may alternatively employ a dedicated pressurized gas supply, such as a pressurized air tank, or other means, effective to supply air or other gas under pressure to inflate the balloon to a predetermined, or desired, extent. A cap 50 may be employed in connection with coupling structure for connection to the gas supply. In like manner, the cap 50 may employ a coupling member 56 at which the feeding tube portion extending into the patient's stomach, is terminated, with a matably engageable coupling member 58 joinable to the coupling member 56. The coupling member 58 thereby is attachable to and detachable from the coupling member 56, to connect or alternatively disconnect the feeding tube, as desired.

As a further embodiment, the balloon 20 may also have a regulator or other gas flow control means (not shown in FIG. 1) associated therewith, to prevent over-inflation of the balloon in the stomach cavity. As yet another variation, the gas tube 18 may have coupled therewith a pressure gauge 60 displaying the pressure in the balloon, and optionally additionally including an indication of the extent of fill of the balloon (e.g., on a scale of 0-100%) so that the inflation gas may be introduced to a desired extent, as regards the volume of the stomach cavity that is desired to be occluded in a given use of the balloon in the inflated state.

Figure 2:
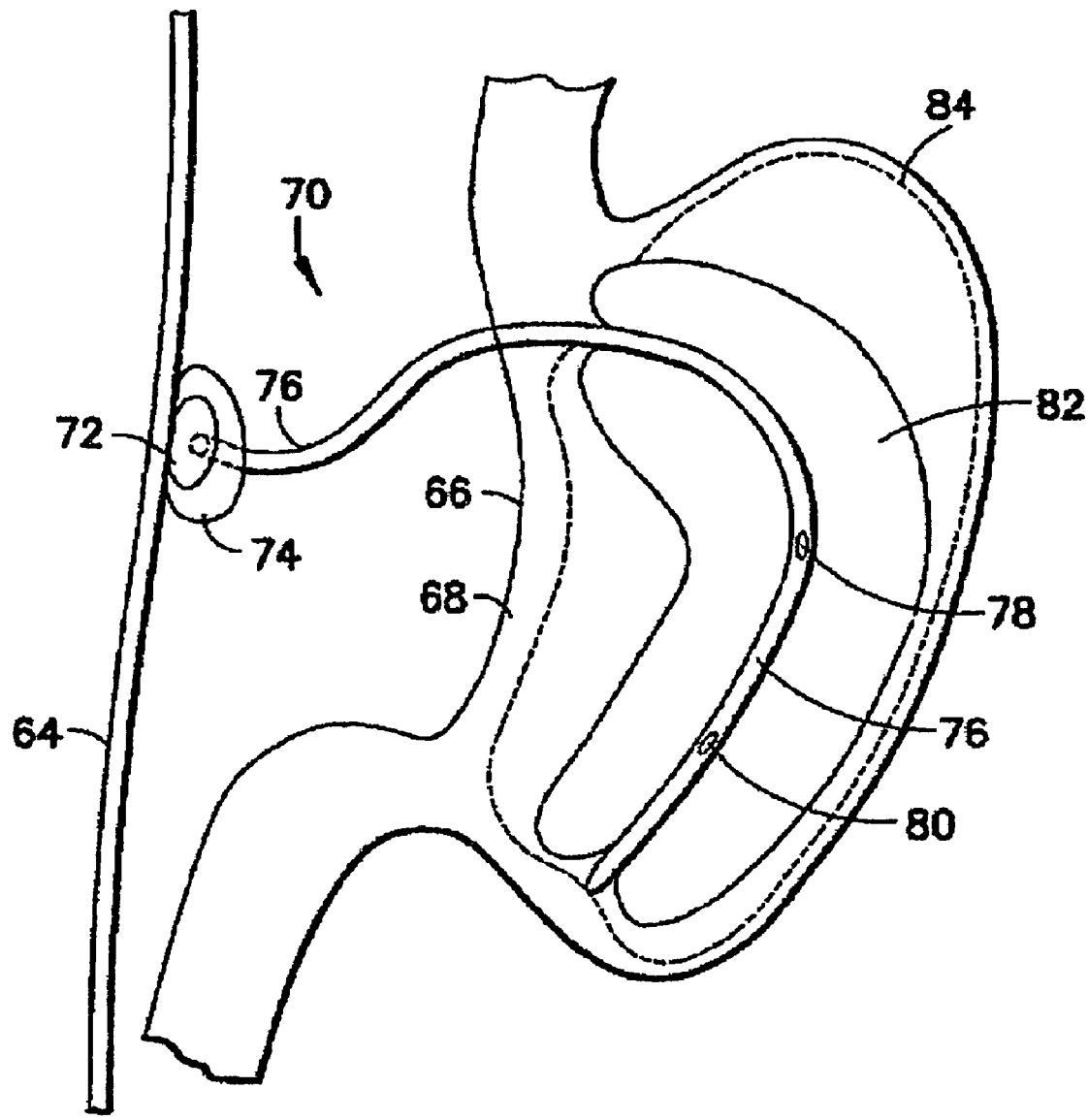
FIG. 2 is a schematic view of a gastro-occlusive device according to another embodiment of the invention.

FIG. 2 is a schematic view of a gastro-occlusive device 70 according to another embodiment of the invention.

The gastro-occlusive device 70 includes a silicone membrane 72 that forms with the associated silicone rubber port member 74 a one-way self-sealing valve that is disposed below the patient's skin 64, as illustrated. The port member 74 in turn communicates with the gas tube (catheter) 76, which passes through the wall of the patient's stomach 66 and into the interior volume 68 of the stomach. The gas tube 76 is circumscribed by an associated balloon 82 shown in the deflated state in solid line representation and in dashed line representation by dashed line 84 in the inflated state.

The balloon 82 is inflated by ingress of gas to the tube 76 from a syringe or gas injector with a penetration element such as a hollow needle that is inserted through the membrane 72, following which air is injected into the port member 74 and flows through the tube 76 into the portion of the tube that is disposed in the stomach of the patient. The injected air flows through gas flow openings 78 and 80 to inflate the balloon 82. Following inflation of the balloon to a desired extent, the syringe or gas injector penetration element is withdrawn from the port member through the membrane 72, which thereupon self-seals, to maintain the inflation pressure in the balloon at a desired level.

Subsequently, if it is desired to deflate the balloon, a hollow penetration element is inserted through the membrane 72 to allow efflux of gas from the balloon and gas tube, through port member 74 and the penetration element. Following deflation, the penetration element is withdrawn from the port member through the membrane, to permit resealing of the membrane to thereafter maintain the balloon in a deflated state.

The balloon and gas tube, as in previously described embodiments, can be formed of any suitable polymeric or other material of construction. For example, these elements may be formed of polyurethane, or alternatively of silicone. Silicone construction of the balloon may require that the balloon be more frequently inflated to compensate for declining pressure, since silicone thin film is typically more gas permeable than polyurethane, but silicone balloons can be employed that hold their pressure, once inflated, for a sustained period of days. For example, in use, wherein silicone balloon construction is utilized, it may be desired for a patient to visit a doctor's office at a periodic interval, for reinflation of the balloon to compensate for the diminution of pressure (and extent of inflation) of the balloon over time, from an initial inflated pressure level.

Since the gastro-occlusive device shown in FIG. 2 is internal, and introduction of inflation gas is by injection through the patient's skin, the cosmetic appearance of the user's body is unaffected, and insertion of the device may be effected by laparoscopic techniques, in an minimally invasive manner, without the potentially severe disadvantages and side effects of stomach stapling procedures.

It will therefore be appreciated that the gastro-occlusive device may be variously configured and accessorized, with or without an associated feeding tube unit, as desired, and that such feeding tube unit when present, may likewise be variously configured and accessorized, to provide a therapeutically effective and reliable apparatus for treatment of morbid obesity and eating disorders of widely varying type.

The gastro-occlusive device of the invention, and the feeding tube unit when employed therewith, may be readily installed in the body of the patient, using minimally invasive laparoscopic techniques for the insertion of the balloon, optional feeding tube, and associated gas tube and anchoring members in the stomach of the patient.

Thus, while the invention has been variously described hereinabove with reference to specific aspects, features and embodiments, it will be recognized that the invention is not thus limited, but rather extends to and encompasses other variations, modifications and alternative embodiments, such as will suggest themselves to those of ordinary skill in the art based on the disclosure herein. Accordingly, the invention is intended to be broadly construed and interpreted, as encompassing all such variations, modifications and alternative embodiments, within the spirit and scope of the claims hereinafter set forth.

What is claimed is:

1. A gastro-occlusive device, comprising:
   a balloon disposable in a stomach cavity of a patient, and inflatable therein to occlude at least 50% of the volume of the stomach cavity, a gas flow tube coupled at a distal end thereof with the balloon and extending through a stomach wall to a proximal end that is at or in interior proximity to a dermal wall of the patient's body or extends exteriorly out of the dermal wall of the patient's body;
   means for selectively inflating the balloon, coupled to the gas flow tube at the proximal end thereof and arranged to flow inflation gas to the balloon in the patient's stomach cavity, for said inflation therein to occlude at least 50% of the volume of the stomach cavity;
   first and second stomach wall positional anchoring members for the gas tube, the first and second positional anchoring members being adapted for placement along inner and outer surfaces, respectively, of a stomach wall of the patient; and
   first and second dermal wall positional anchoring members for the gas tube, the first and second dermal wall positional anchoring members being adapted for placement along outer and inner surfaces, respectively, of the dermal wall;
   wherein spacing is provided between said second stomach wall positional anchoring member and said second dermal wall positional anchoring member with a section of the gas tube extending therebetween to allow occurrence of normal movement of the stomach wall and normal movement of the dermal wall relative to one another adjacent to the stomach wall positional anchoring members and dermal wall positional anchoring members.

2. The gastro-occlusive device of claim 1, wherein said balloon is formed of a thin film polymeric material.

3. The gastro-occlusive device of claim 2, wherein said polymeric material comprises a material selected from the group consisting of polyurethane and silicone.

4. The gastro-occlusive device of claim 1, wherein the proximal end of the gas flow tube is joined to a cap at the surface of the patient's body, and said cap includes coupling members to which the means for selectively inflating the balloon are connected.

5. The gastro-occlusive device of claim 1, wherein the proximal end of the gas flow tube is coupled exteriorly of the patient's body to said means for selectively inflating the balloon.

6. The gastro-occlusive device of claim 1, wherein the means for selectively inflating the balloon are selected from the group consisting of a manually operable squeeze bulb and a pressurized gas supply.

7. The gastro-occlusive device of claim 1, wherein the means for selectively inflating the balloon are arranged for selectively deflating the balloon subsequent to selectively inflating it.

8. The gastro-occlusive device of claim 1, in combination with a feeding tube unit, wherein the feeding tube unit comprises a nutritive fluid supply coupled with a feeding tube, and the feeding tube is arranged with its distal end disposed in the stomach cavity of the patient.

9. The gastro-occlusive device of claim 8, wherein the feeding tube is interiorly disposed in the gas flow tube with the body of a patient.

10. The gastro-occlusive device of claim 1, wherein the balloon when inflated occupies about 50% to about 100% of total volume of the stomach cavity of a patient.

11. The gastro-occlusive device of claim 1, wherein the balloon when inflated occupies at least 95% of total volume of the stomach cavity of a patient.

12. A method of treating a subject in need of treatment for an eating disorder or overweight condition, said method comprising disposing in the stomach of the subject a balloon that is inflatable to occlude at least 50% of interior volume of the stomach, wherein the balloon is coupled by a tube defining a gas flow passage to an actuatable source of inflation gas, and actuating the source of inflation gas to flow gas into the balloon for inflation thereof to occlude at least 50% of the interior volume of the stomach, to an extent producing satiety with reduced intake of nutrition, relative to a corresponding subject lacking the inflated balloon in the subject's stomach, wherein the stomach is defined by a stomach wall, said gas flow passage is at or in interior proximity to a dermal wall of the subject's body or extends exteriorly out of the dermal wall of the subject's body, wherein the tube is anchored to the stomach wall with first and second stomach wall positional anchoring members adapted for placement along inner and outer surfaces, respectively, of the stomach wall; wherein the tube is anchored to the dermal wall with first and second dermal wall anchoring members disposed along outer and inner surfaces, respectively, of the dermal wall; wherein spacing is provided between said second stomach wall positional anchoring member and said second dermal wall positional anchoring member with a section of the tube extending therebetween, with the spacing allowing occurrence of normal movement of the stomach wall and normal movement of the dermal wall relative to one another adjacent to the stomach wall positional anchoring members and the dermal wall positional anchoring members.

13. The method of claim 12, wherein the balloon when inflated occupies about 50% to about 100% of total volume of the stomach cavity of a patient.

14. The method of claim 12, wherein the balloon is inflated to occlude at least 95% of total volume of the subject's stomach.

15. The method of claim 12, wherein the subject's stomach is supplied by a feeding tube with nutrition.

16. The method of claim 15, wherein the nutrition is supplied when the balloon is in a deflated state.

17. The method of claim 15, wherein the nutrition is supplied when the balloon is in an inflated state.

18. A gastro-occlusive device, comprising:
a balloon disposable in a stomach cavity of a patient, and inflatable therein to occlude at least 50% of the volume of the stomach cavity, a gas flow tube coupled at a distal end thereof with the balloon and extending through a stomach wall to a proximal end that is at or in interior proximity to a surface of the patient's body or extends exteriorly out of a dermal wall of the patient's body;
means for selectively inflating the balloon, coupled to the gas flow tube at the proximal end thereof and arranged to flow inflation gas to the balloon in the patient's stomach cavity, for said inflation therein to occlude at least 50% of the volume of the stomach cavity;
an inner stomach wall positional anchoring member for the gas tube, said inner stomach wall positional anchoring member being adapted for placement along an inner surface of a stomach wall of the patient;
an outer dermal wall positional anchoring member for the gas tube, said outer dermal wall positional anchoring member being adapted for placement along an outer surface of the dermal wall; and
at least one additional positional anchoring member including any of (i) an outer stomach wall positional anchoring member for the gas tube, said outer stomach wall positional anchoring member being adapted for placement along an outer surface of a stomach wall of the patient, and (ii) an inner dermal wall positional anchoring member for the gas tube, said inner dermal wall positional anchoring member being adapted for placement along an inner surface the dermal wall;
wherein spacing is provided between the stomach wall and the dermal wall adjacent to said at least one additional positional anchoring member, with a section of the gas tube extending between the stomach wall and the dermal wall to allow occurrence of normal movement of the stomach wall and normal movement of the dermal wall relative to one another adjacent to the at least one additional positional anchoring member.

19. The gastro-occlusive device of claim 18, in combination with a feeding tube unit, wherein the feeding tube unit comprises a nutritive fluid supply coupled with a feeding tube, and the feeding tube is arranged with its distal end disposed in the stomach cavity of the patient.

20. A method of treating a subject in need of treatment for an eating disorder or overweight condition, said method comprising disposing in the stomach of the subject a balloon that is inflatable to occlude at least 50% of interior volume of the stomach, wherein the balloon is coupled by a tube defining a gas flow passage to an actuatable source of inflation gas, and actuating the source of inflation gas to flow gas into the balloon for inflation thereof to occlude at least 50% of the interior volume of the stomach, to an extent producing satiety with reduced intake of nutrition, relative to a corresponding subject lacking the inflated balloon in the subject's stomach;
wherein the stomach is defined by a stomach wall, said gas flow passage is at or in interior proximity to a dermal wall of the subject's body or extends exteriorly out of the dermal wall of the subject's body;
wherein the tube is anchored to the stomach wall and the dermal wall via elements including (A) an inner stomach wall positional anchoring member arranged along an inner surface of the stomach wall, (B) an outer dermal wall anchoring member arranged along an outer surface of the dermal wall, and (C) at least one additional positional anchoring member including any of (i) an outer stomach wall positional anchoring member arranged along an outer surface of the stomach wall and (ii) an inner dermal wall positional anchoring member arranged along an inner surface of the dermal wall; and
wherein spacing is provided between the stomach wall and the dermal wall adjacent to said at least one additional positional anchoring member, with a section of the tube extending between the stomach wall and the dermal wall to allow occurrence of normal movement of the stomach wall and normal movement of the dermal wall relative to one another adjacent to the at least one additional positional anchoring member.

* * * * *

UNITED STATES PATENT AND TRADEMARK OFFICE
CERTIFICATE OF CORRECTION

| | |
|---|---|
| PATENT NO. | : 7,470,251 B2 |
| APPLICATION NO. | : 11/273065 |
| DATED | : December 30, 2008 |
| INVENTOR(S) | : Tilak M. Shah |

It is certified that error appears in the above-identified patent and that said Letters Patent is hereby corrected as shown below:

Column 1, lines 3-4: "CROSS-REFERENCE TO RELATED APPLICATIONS" should be -- CROSS REFERENCE TO RELATED APPLICATION --.

Column 3, line 19: "POLYMERIC FThM" should be -- POLYMERIC FILM --.

Column 3, line 28: "U.S. Pa. No. 6,460,541" should be -- U.S. Pat. No. 6,460,541 --.

Column 4, line 31: "members, insert adapted" should be -- members, adapted --.

Signed and Sealed this

Thirty-first Day of March, 2009

JOHN DOLL
*Acting Director of the United States Patent and Trademark Office*